US009867391B2

(12) United States Patent
Dardevet et al.

(10) Patent No.: US 9,867,391 B2
(45) Date of Patent: Jan. 16, 2018

(54) ACCELERATING MUSCLE RECOVERY AFTER IMMOBILIZATION-INDUCED MUSCLE ATROPHY

(71) Applicants: NESTEC S.A., Vevey (CH); INSTITUT NATIONAL DE LA RECHERCHE AGRONOMIQUE (INRA), Paris (FR)

(72) Inventors: Dominique Dardevet, Aubiere (FR); Isabelle Savary-Auzeloux, Clermont-Ferrand (FR); Didier Remond, Aydat (FR); Lydie Combaret, Les Martres de Veyre (FR); Gary Williamson, Harrogate Yorkshire (GB); Magali Faure, Forel (CH); Denis Breuille, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/350,709

(22) PCT Filed: Oct. 11, 2012

(86) PCT No.: PCT/EP2012/070121
§ 371 (c)(1),
(2) Date: Apr. 9, 2014

(87) PCT Pub. No.: WO2013/053795
PCT Pub. Date: Apr. 18, 2013

(65) Prior Publication Data
US 2014/0255511 A1 Sep. 11, 2014

(30) Foreign Application Priority Data
Oct. 11, 2011 (EP) .................................... 11184580

(51) Int. Cl.
A61P 21/00 (2006.01)
A61K 31/353 (2006.01)
A61K 31/198 (2006.01)
A23L 33/175 (2016.01)
A23L 1/305 (2006.01)
A61K 31/12 (2006.01)
A61K 31/355 (2006.01)
A61K 31/7048 (2006.01)
A61K 33/04 (2006.01)
A61K 33/30 (2006.01)
A23K 20/174 (2016.01)
A23K 20/111 (2016.01)
A23K 20/142 (2016.01)
A23K 20/20 (2016.01)
A23L 33/15 (2016.01)
A23L 33/155 (2016.01)
A23L 33/16 (2016.01)
A23L 33/17 (2016.01)

(52) U.S. Cl.
CPC .......... A23L 1/3051 (2013.01); A23K 20/111 (2016.05); A23K 20/142 (2016.05); A23K 20/174 (2016.05); A23K 20/30 (2016.05); A23L 33/15 (2016.08); A23L 33/155 (2016.08); A23L 33/16 (2016.08); A23L 33/17 (2016.08); A23L 33/175 (2016.08); A61K 31/12 (2013.01); A61K 31/198 (2013.01); A61K 31/353 (2013.01); A61K 31/355 (2013.01); A61K 31/7048 (2013.01); A61K 33/04 (2013.01); A61K 33/30 (2013.01); A23V 2002/00 (2013.01); A23V 2200/316 (2013.01); A23V 2250/0628 (2013.01); A23V 2250/1626 (2013.01); A23V 2250/1642 (2013.01); A23V 2250/214 (2013.01); A23V 2250/2112 (2013.01); A23V 2250/2116 (2013.01); A23V 2250/2117 (2013.01); A23V 2250/702 (2013.01); A23V 2250/712 (2013.01)

(58) Field of Classification Search
None
See application file for complete search history.

(56) References Cited

U.S. PATENT DOCUMENTS 6,589,948 B1 * 7/2003 Malfroy-Camine et al. . 514/185
2004/0097404 A1 * 5/2004 Kessler et al. .................... 514/2
2007/0129428 A1 * 6/2007 Richelle et al. .............. 514/456
(Continued)

FOREIGN PATENT DOCUMENTS

JP 2003073279 3/2003
JP 2007039349 2/2007
(Continued)

OTHER PUBLICATIONS

Nielson, "Bioavailability Is Improved by Enzymatic Modification of the Citrus Flavonoid Hesperidin in Humans: A Randomized, Double-Blind, Crossover Trial1", The Journal of Nutrition, vol. 136, No. 2, 404-408, Feb. 2006.*
Cho, "Antioxidant and Neuroprotective Effects of Hesperidin and its Aglycone Hesperetin", Archives of Pharmacal Research, vol. 29, No. 8, 669-706, 2006.*
Appell et al., "Supplementation of Vitamin E May Attenuate Skeletal Muscle Immobilization Atrophy" Int. J Sports Med., 1997, vol. 18, pp. 157-160. XP002667635.
Marzani et al., "Antioxidant supplementation restores defective leucine stimulation of protein synthesis in skeletal muscle from old rats" The Journal of Nutrition, 2008, vol. 138, pp. 2205-2211.
Verhoeven et al., "Long-term leucine supplementation does not increase muscle mass or strength in healthy elderly men" The American Journal of Clinical Nutrition, 2009, vol. 89, pp. 1468-1475.
(Continued)

Primary Examiner — Robert T. Crow
Assistant Examiner — John P Nguyen
(74) Attorney, Agent, or Firm — K&L Gates LLP

(57) ABSTRACT

The present invention generally relates to the field of medical nutrition. For example, the present invention provides a composition that can be used to treat, prevent and/or reverse muscle atrophy related to immobilization and its consequences. One embodiment of the present invention concerns a composition comprising a leucine and antioxidants that can be used in accelerating muscle recovery after muscle atrophy.

20 Claims, 7 Drawing Sheets

(56) References Cited

U.S. PATENT DOCUMENTS

| | | | |
|---|---|---|---|
| 2007/0280997 A1 | 12/2007 | Portman | |
| 2008/0069834 A1* | 3/2008 | Zicker et al. | 424/195.17 |
| 2008/0254130 A1* | 10/2008 | Gupta | 424/489 |
| 2009/0117197 A1* | 5/2009 | Bascomb | A61K 31/138 424/523 |
| 2009/0281174 A1 | 11/2009 | Ota et al. | |
| 2010/0041746 A1* | 2/2010 | D'Orazio | A23L 1/30 514/456 |

FOREIGN PATENT DOCUMENTS

| | | |
|---|---|---|
| JP | 2009209066 | 9/2009 |
| JP | 2011512798 | 4/2011 |
| WO | WO2008004340 A1 | 1/2008 |
| WO | 2011011252 | 1/2011 |
| WO | 2011078654 | 6/2011 |

OTHER PUBLICATIONS

Chopard et al., "Molecular events and signalling pathways involved in skeletal muscle disuse-induced atrophy and the impact of countermeasures" Journal of Cellular and Molecular Medicine, 2009, vol. 13, pp. 3032-3050.

Baptista et al., "Leucine attenuates skeletal muscle wasting via inhibition of ubiquitin ligases" Muscle & Nerve, 2010, vol. 41, pp. 800-808.

Vazeille et al., "Curcumin treatment prevents increased proteasome and apoptosome activities in rat skeletal muscle during reloading and improves subsequent recovery" The Journal of Nutritional Biochemistry, 2012, vol. 23, pp. 245-251.

Japanese Office Action for Application No. P2014-535068, Dispatch No. 234201, Dispatch Date May 31, 2016, 8 pages.

Japanese Office Action Appl. No. P2014-535068 dated Mar. 28, 2017 2 pages (English Translation).

Japanese Office Action Appl. No. P2014-535068 dated Mar. 28, 2017 6 pages.

* cited by examiner

Diet Composition and Mineral and Vitamin Mix composition

| g/kg diet | Standard diet (C) = Casein 13% diet | Standard diet (C) + ALA = Casein 13% + Alanine | Standard diet (C) + AOX = Casein 13% + AOX | Standard diet (C) + AOX + LEU = 13% Casein diet + AOX + Leucine | Standard diet (C) + LEU = Casein 13% diet + Leucine |
|---|---|---|---|---|---|
| Casein | 166 | 166 | 166 | 166 | 166 |
| L Cystine | 1,8 | 1,8 | 1,8 | 1,8 | 1,8 |
| Alanine |  | 59 |  |  |  |
| Rapeseed oil | 30 | 30 | 30 | 30 | 30 |
| Sunflower oil | 3 | 3 | 3 | 3 | 3 |
| Grounnut oil | 27 | 27 | 27 | 27 | 27 |
| Cellulose | 35 | 35 | 28,57 | 28,57 | 28,57 |
| Saccharose | 100 | 100 | 100 | 100 | 100 |
| Lactose | 134 | 134 | 134 | 134 | 134 |
| Wheat starch | 458,2 | 399,2 | 458,2 | 398,8 | 398,8 |
| AIN 93M mineral mix | 35 | 35 |  |  | 35 |
| Control vitamin mix | 10 | 10 |  |  | 10 |
| Hesperetin 7 glucoside |  |  | 1 | 1 |  |
| Curcumin |  |  | 1,43 | 1,43 |  |
| Green tea catechin |  |  | 2 | 2 |  |
| Rutin |  |  | 2 | 2 |  |
| Leucine |  |  |  | 44,5 | 44,5 |
| Isoleucine |  |  |  | 5,1 | 5,1 |
| Valine |  |  |  | 9,8 | 9,8 |
| Supplemented mineral mix |  |  | 35 | 35 |  |
| Supplemented vitamin mix |  |  | 10 | 10 |  |

FIG. 6

|  | Control Vitamin Mix | Supplemented Vitamin Mix |
|---|---|---|
|  | g or UI / kg | g or UI / kg |
| Nicotinic acid | 3 | 3 |
| D-pantothenate Ca | 1,6 | 1,6 |
| Pyridoxine HCl | 0,7 | 0,7 |
| Thiamin HCl | 0,6 | 0,6 |
| Riboflavin | 0,6 | 0,6 |
| Acide folique | 0,2 | 0,2 |
| D-biotin | 0,02 | 0,02 |
| Vit B12 (0.1%) | 2,5 | 2,5 |
| Acetate di-alpha-tocophérol Vit E | 1000 UI | 30 000 UI |
| Vitamine A | 400 000 UI | 800 000 UI |
| Vitamine D3-cholécalciférol | 100 000 UI | 100 000 UI |
| Vitamine K | 0,075 | 0,075 |
| Cholin (chlorhydrate, bitartrate) | 250 | 250 |
| Starch | Up to 1000 g | Up to 1000 g |

|  | AIN 93M Mineral Mix | Supplemented Mineral Mix |
|---|---|---|
|  | g or UI / kg | g or UI / kg |
| Calcium Carbonate | 375 | 375 |
| Mono Potassic Phosphate | 250 | 250 |
| NaCl | 74 | 74 |
| Potassium Sulfate | 46,6 | 46,6 |
| Potassium Citrate 1 H2O | 28 | 28 |
| Mg Oxide | 24 | 24 |
| Ferric Citrate | 6,06 | 6,06 |
| Zinc Carbonate | 1,65 | 2,73 |
| Manganese Carbonate | 0,63 | 0,63 |
| Copper Carbonate | 0,3 | 0,3 |
| Potassium Lodure | 0,01 | 0,01 |
| Sodium Selenite anhydre | 0,01025 | 0,01429 |
| Ammonium Molybdate 4 H2O | 0,00795 | 0,00795 |
| Na Metasiliate, 9 H2O | 1,45 | 1,45 |
| Chrome Sulfate, potassium 12H2O | 0,0275 | 0,0275 |
| Boric acid | 0,0815 | 0,0815 |
| Na Fluorure | 0,0635 | 0,0635 |
| Ni Carbonate | 0,0318 | 0,0318 |
| Lithium Chloride | 0,0174 | 0,0174 |
| Ammonium Vanadate | 0,0066 | 0,0066 |
| Starch | Up to 1000 g | Up to 1000 g |

FIG. 7

ACCELERATING MUSCLE RECOVERY AFTER IMMOBILIZATION-INDUCED MUSCLE ATROPHY

CROSS REFERENCE TO RELATED APPLICATIONS

The present application is a National Stage of International Application No. PCT/EP2012/070121, filed on Oct. 11, 2012, which claims priority to European Patent Application No. 11184580.6, filed Oct. 11, 2011, the entire contents of which are being incorporated herein by reference.

The present invention generally relates to the field of medical nutrition. For example, the present invention provides a composition that can be used to treat and/or reverse muscle atrophy and its consequences. One embodiment of the present invention concerns a composition comprising leucine and antioxidant nutrients that can be used in accelerating muscle recovery after muscle atrophy.

Skeletal muscle is a highly plastic muscle. Muscle hypertrophies during strength training and increases its oxidative capacity in response to endurance training. By contrast, skeletal muscle atrophies in numerous conditions e.g., diseases, ageing, or loss of physical activity.

In addition, bed rest and/or immobilization is often the selected treatment of musculoskeletal injuries, and further causes degenerative changes that often lead to additional atrophy. Moreover, bed rest is a mandatory state associated with various diseases and the low physical activity related to bed rest is responsible for dramatic muscle losses.

Muscle wasting results from an imbalance between protein synthesis and breakdown rates but also from an imbalance between apoptotic and differentiation/regeneration processes. Muscle proteins can be catabolized into free amino acids (AA) that are used to provide substrates to synthesize protein in other organs for the host defense in the case of various pathologies or stressful events. Thus, the main function of skeletal muscle is to provide power and strength for locomotion and posture, but muscle is also the major reservoir of proteins and amino acids in the body. Consequently, an uncontrolled and sustained muscle wasting impairs human movement, leads to difficulties in performing daily activities and has detrimental metabolic consequences.

The recovery of muscle mass following the insult and/or muscle disuse is then critical to maintain autonomy.

Although physical interventions, such as exercise were shown to be beneficial, they are not always applicable to all situations in particular when muscle inactivity results from a wound, a traumatism or a weakening pathology.

Consequently, there is a need for additional strategies such as nutritional strategies to improve muscle recovery.

The present inventors have addressed this need.

Hence, it was the objective of the present invention to improve the state of the art and to provide the art with a composition that can effectively be used to accelerate skeletal muscle recovery after muscle atrophy caused by immobilization.

The present inventors were surprised to see that they could achieve this objective by the subject matter of the independent claims. The subject matter of the dependent claims further develops the idea of the present invention.

The present inventors have tested if nutritional supports during immobilization and the recovery period (after immobilization) can limit muscle atrophy and/or favour muscle protein recovery.

They have used as a rat immobilization model, a hindlimb immobilization casting using an orbi-soft plaque (Gibaud, France). This model was chosen because it is reversible and then the recovery period can be tested.

The inventors were able to demonstrate that a diet rich in antioxidant nutrients and leucine speeds up the recovery of muscle mass of immobilized muscles.

Consequently, the present invention relates to a composition comprising leucine in an amount of between 2 and 10 weight-% based on total dry weight of the composition and at least one antioxidant for use in the treatment or prevention of muscle atrophy, in particular in accelerating muscle recovery after muscle atrophy.

The present invention also relates to the use of between 2 and 10% weight leucine and at least one antioxidant for the preparation of a composition in the treatment or prevention of muscle atrophy, in particular in accelerating muscle recovery after muscle atrophy.

The present invention further relates to a composition comprising leucine in an amount of between 2 and 10 weight-% based on total dry weight of the composition and at least one antioxidant for use in the treatment or prevention of muscle atrophy caused by immobilization As antioxidants any antioxidant may be used. Preferred are food grade antioxidants. A compound is considered food-grade if it is generally accepted and considered safe for food applications.

Mixtures of antioxidants may be used. For example antioxidants may be provided as food compositions that are known to be rich in antioxidants or as extracts thereof.

Being rich in antioxidants usually means having a ORAC (oxygen radical absorbance capacity) rating of 1000 per 100 g.

The United States Department of Agriculture has published an article that assesses the oxygen radical Absorbance Capacity (ORAC) of Selected Foods [Oxygen Radical Absorbance Capacity (ORAC) of Selected Foods-2007, from the United States Department of Agriculture].

Cocoa, coffee or tea are high in antioxidants.

Several spices or herbs may also be used such as oregano, cumin, ginger, garlic, coriander, onion, thyme, marjoram, tarragon, peppermint, and/or basil.

Fruit extracts or dried fruits may be used. Examples are pears, apples, raisins, figs, dates, cranberries, blueberries, blackberries, raspberries, strawberries, blackcurrants, cherries, oranges, mango, and/or pomegranates.

As vegetables high in antioxidants cabbage, broccoli, beetroot and spinach may be listed.

Antioxidants may also be used as purified compounds or partially purified compounds.

Accordingly, the at least one antioxidant may be selected from the group consisting of hesperetine-7-glucoside, curcumin, green tea catechins, rutin, vitamin E, vitamin A, Zn, Se or combinations thereof.

Metabolites of these antioxidants may be used.

Muscle atrophy may have many reasons. It may result from immobilization or low physical activity, e.g., associated with age (sarcopenia associated with ageing process) or from several co-morbidities of diseases, such as cancer, AIDS, congestive heart failure, COPD (chronic obstructive pulmonary disease), renal failure, trauma, sepsis, and severe burns, for example. Muscle atrophy may also result from insufficient or inappropriate nutrition or starvation, for example.

Very commonly, muscle atrophy results from disuse or insufficient use of the respective muscle.

This is often the case for hospitalized patients and/or patients with broken bones, for example, and/or where a patient is fully or partially immobilized.

Consequently, in the present invention muscle atrophy is caused by immobilization. This immobilization may be caused by bed rest and/or by plastering. Immobilization may be complete or partial. A partial immobilization allows some movement but insufficient to sustain the complete muscle tissue.

The causes of sarcopenia are multifactorial and can include disuse, changing endocrine function, chronic diseases, inflammation, insulin resistance and nutritional deficiencies (Fielding et al, J. Am Med. Dir. Assoc. 2011, 12:249-256).

The many possible underlying physiological reasons for muscle loss have as a consequence that different therapies are required for each reason. For example, there are some reports that ageing can be associated with sarcopenia defined as the age-associated loss of skeletal muscle mass and function. Studies have shown that the addition of leucine to the meal of elderly sarcopenic patients may be beneficial to treat sarcopenia. Recent work from Kastanos et al (Am J. Physiol. Endocrinol. Metab. 291:E381-E387, 2006) has clearly shown that additional of leu in the diet did not increased muscle protein synthesis in young subjects while the same leucine supplementation was efficient in elderly. These authors concluded that elderly people exhibit a decrease sensitivity of muscle protein synthesis to leucine that is not observed in young adults.

Thus, the mechanisms involved in treating or preventing age-associated sarcopenia are different from treating or preventing muscle mass losses associated with immobilization alone and—consequently—it was expected that the a successful treatment or prevention of non-ageing associated muscle mass loss must be carried out differently than in elderly patients.

The inventors were surprised to see that they could use leucine supplementation also to treat or prevent immobilization-related muscle mass loss.

The inventors have found that a combination of leucine and at least one antioxidant is very effective in achieving the object of the present invention.

Leucine may be provided as free leucine or as a protein source containing high a level of leucine. Such a protein source may be whey protein, for example.

Leucine and the at least one antioxidant were found to act synergistically.

Without wishing to be bound by theory, the inventors presently believe that leucine supplementation improves post prandial muscle protein synthesis and speeds up recovery, while antioxidant supplementation potentiates the anabolic effect of leucine, preserves muscle mass, decreases apoptosis and contributes to a more rapid normalization of apoptosis and proteolysis.

Good results were obtained with a composition comprising leucine and at least one antioxidant in a weight ratio in the range of 25:1 to 1:1, for example of about 17:1 to 2:1.

The composition may comprise about 20-100 g leucine per kg of the composition, for example about 25-60 g leucine per kg of the composition.

In therapeutic applications, compositions are administered in an amount sufficient to at least partially cure or arrest the symptoms of the disease and its complications. An amount adequate to accomplish this is defined as "a therapeutically effective dose". Amounts effective for this purpose will depend on a number of factors known to those of skill in the art such as the severity of the disease and the weight and general state of the patient.

In prophylactic applications, compositions according to the invention are administered to a patient susceptible to or otherwise at risk of a particular disease in an amount that is sufficient to at least partially reduce the risk of developing a disease. Such an amount is defined to be "a prophylactically effective dose". Again, the precise amounts depend on a number of patient specific factors such as the patient's state of health and weight.

The compositions of the present invention are to be administered in a therapeutically effective dose or in a prophylactically effective dose.

Both, the therapeutically effective dose or the prophylactically effective dose can be determined by those of skill in the art.

For example, the composition may to be administered in an amount corresponding to about 0.03 to 0.2 g leucine per kg body weight.

The leucine may be selected from D- or L-leucine. Preferred is the natural L-form.

For example, the composition may comprise about 20-100 g leucine per kg of the composition, for example 25-60 g leucine per kg of the composition.

All three branched chain amino acids (BCAAs), leucine valine and isoleucine share common enzymes for the first 2 degradative steps, transamination and subsequent decarboxylation, and are also the only indispensable amino acids to have degradative metabolic pathways active in muscle. Therefore, it could be hypothesized that given a large dose of a single BCAA (e.g. leucine) may cause the decarboxylation/oxidation of the other two BCAAs (e.g. isoleucine & valine), causing them to become limiting for muscle protein synthesis—especially in situations where leucine may be 'spiked'. Indeed, a study by Verhoeven and colleagues (Am J Clin Nutr. 2009 May;89(5):1468-75), also found that leucine supplementation resulted in an approximate 15 and 25% decreases in isoleucine and valine, respectively. In this context, it will be beneficial to add valine and isoleucine in addition to leucine into the composition, thus avoiding a depletion of valine and isoleucine circulating concentration secondary to leucine level.

For the same reason, it is not recommended and may be harmfull to administer large amount of leucine which may induce the decrease of other branched amino acids i.e. valine and isoleucine. Thus it was one objective of the present invention to administer leucine in an amount as low as possible, while still having a remarkable effect in accelerating muscle recovery after muscle atrophy.

Thus the present inventors recommend a maximum dose of leucine at 10 wt % of the dry matter of the composition The composition may be supplemented with valine and/or isoleucine.

For example the composition may comprise about 10-50 g valine per kg of the composition, for example 15-30 g valine per kg of the composition. The composition may also comprise about 10-50 g isoleucine per kg of the composition, for example 15-30 g isoleucine per kg of the composition.

The composition of the present invention is most effective when it is administered consecutively for a number of days, ideally until complete muscle recovery is achieved.

For example, the composition of the present invention may be to be administered daily during a period for at least 14, 21, 30, 60 or 90 consecutive days.

The ideal duration of the administration of the composition of the present invention may be determined by those of skill in the art.

The compositions of the present invention can be administered during or immediately following immobilization. They may be to be administered from the beginning of the recovery period following the immobilization period.

For example, the compositions of the present invention may be to be administered immediately following immobilization. This way, the positive effect of the composition of the present invention on muscle recovery is additionally supported by physical exercise of the muscle after immobilization.

The composition of the present invention is effective when it is ingested. Hence, it is preferred if the composition is administered orally or enterally, for example via tube feeding.

Alternatively, in more severe cases where an oral or enteral administration is not possible or not advised as it may be the case for specific clinical circumstances, the composition of the present invention may also be to be administered parenterally.

The composition may be to be administered to humans or animals, for example pet animals. Also pet animals may suffer from muscle atrophy after injuries and/or operation and the ability to use their muscles properly is critical for their life quality and full recovery.

The composition of the present invention may be any kind of composition that is suitable for human and/or animal consumption.

For example, the composition may be selected from the group consisting of food compositions, dietary supplements, nutritional compositions, nutraceuticals, powdered nutritional products to be reconstituted in water or milk before consumption, food additives, medicaments, drinks, and pet food.

By consuming the composition of the present invention essentially the recovery of every muscle can be supported after atrophy.

Preferably, the muscle is a skeletal muscle.

For example, the composition of the present invention may be used to support the recovery of muscles of arms and/or legs.

For example, the muscle may be selected from the group consisting of gastrocnemius, tibialis, soleus, extensor digitorum longus (EDL), biceps femoris, semitendinosus, semimembranosus, gluteus maximus or combinations thereof.

A typical composition of the present invention may be a food composition and may comprise per kg
 0.5-1.5 g hesperetine-7-glucoside
 1-2 g curcumin
 1-3 g green tea catechins
 1-3 g rutin
 Vitamin E: 300 IU
 Vitamin A: 8000 IU
 Selenium: 4-6 µg
 Zinc: 90-100 µg
 40-50 g L-leucine
 3-8 g L-valine, and
 8-12 g L-isoleucine.

Another typical composition of the present invention may be a food composition and may comprise per kg
 20 g whey protein
 0.5 g curcumin
 0.5 g rutin
 2 g of polyunsaturated fatty acids Another typical composition of the present invention may be a food composition and may comprise per kg
 300 g/kg whey protein
 170 g/kg lipids
 500 g/kg carbohydrate
 20 g free leucine
 2.5 g free valine
 3.0 g free isoleucine
 5 g antioxidants taken from the group of Hesperetine-7-glucoside, curcumin, green tea catechins, rutin, vitamin E, vitamin A, Zn, Se Those skilled in the art will understand that they can freely combine all features of the present invention described herein, without departing from the scope of the invention as disclosed. In particular, features described for the composition of the present invention may be applied to the use of the present invention and vice versa.

Further advantages and features of the present invention are apparent from the following Examples and Figures.

FIGS. 6 and 7 are tables showing diet composition and mineral and vitamin mix compositions used in the experiment examples disclosed herein.

EXAMPLES

Rats' hindlimb were immobilized using an orbi-soft plaque for 8 days (I0 to I8) (the controlateral hindlimb which is not immobilized is considered as a control on the same animal).

Immobilization leads to muscle wasting induced by a localized alteration of muscle protein metabolism in the hindlimb. The intensity of the muscle wasting and the metabolic parameters explaining the muscle loss (protein synthesis/proteolysis) were measured before and after the immobilization period. The capacity of the previously immobilized hindlimb to recover was measured over 40 days after cast removal at different time points (animals slaughtered at R10, R15, R20, R30, R40) days after the end of the immobilization period).

The beneficial effect of antioxidant supplements (AOX: hesperetine-7-glucoside, curcumin, green tea catechins, rutin, Vitamin E, Vitamin A, Selenium, Zinc) associated with leucine (LEU) in the diets on muscle atrophy during the immobilization and during the recovery period was tested using 2 groups of animals: one group immobilized fed with a standard diet (C) and one group fed with the AOX diet during the immobilization period (I0 to I8), then with AOX and LEU combined within the diet from I8 to R15 and finally with LEU diet from R15 to R40. All diets were isoenergetic and when leucine was present in the supplemented diets, alanine was added at the same amount in the corresponding control diets in either the immobilized and pair-fed groups in order to be isonitrogeneous (Table 1). Furthermore, in order to prevent the fall of valine and isoleucine consequently to the plasma leucine elevation, LEU diets were supplemented with valine and isoleucine, not to increase their plasma concentrations but to prevent their decrease during the experimental period.

Because immobilization leads to a food intake reduction, one group of pair fed (PF) animals (to the immobilized animals) receiving a C diet allowed demonstrating the impact of immobilization alone on muscle protein metabolism.

Lastly, at each time-point, animals were slaughtered either in the post-prandial or post-absorptive state because protein metabolism is highly dependant on the nutritional state of the animals.

337 Male Wistar rats (6-8 month-old and weighing about 400-500 g.) were used in this experiment (supplier: Janvier Company).

9 animals per experimental group, per time and nutritional state were slaughtered. The nutritional state corresponds to the post absorptive (PA) and post prandial (PP) state.

Figure 1:
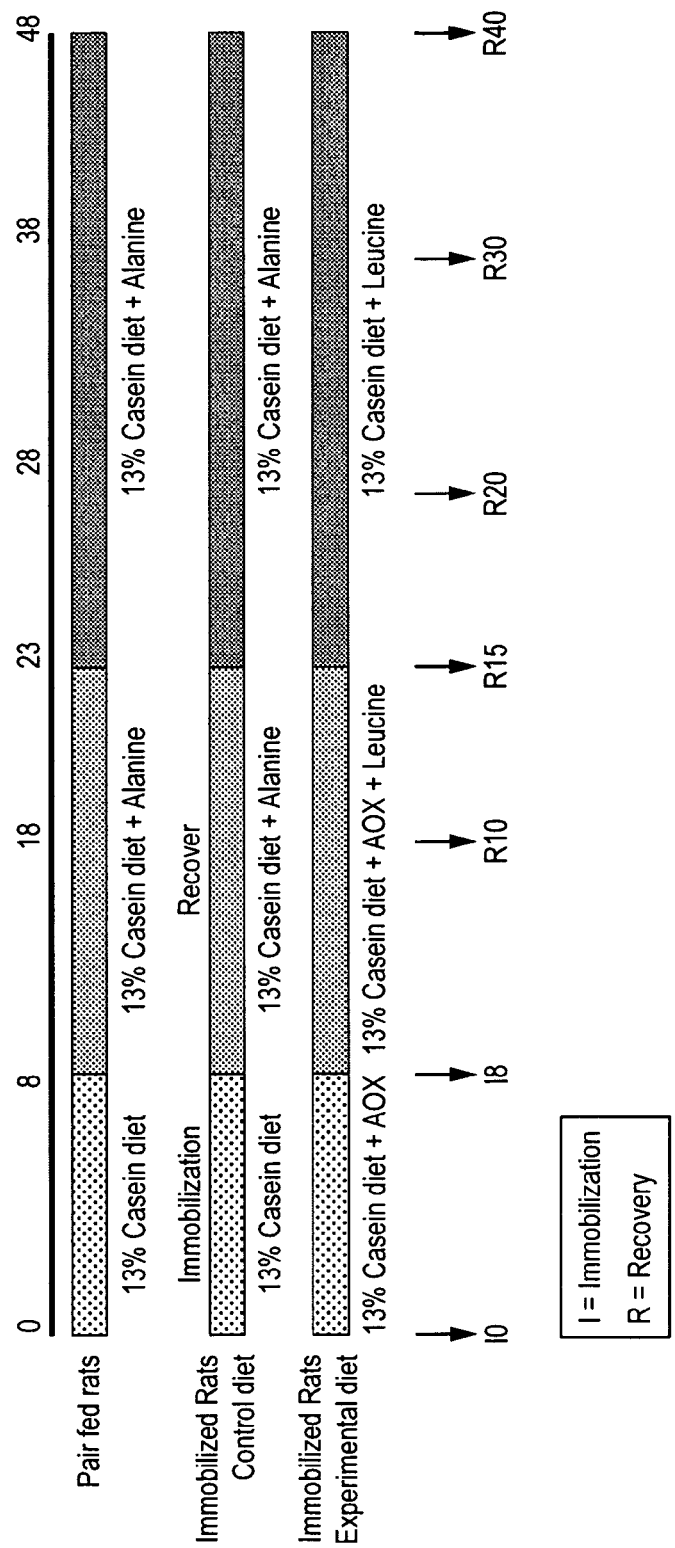
FIG. 1 shows the experimental design.
Figure 2:
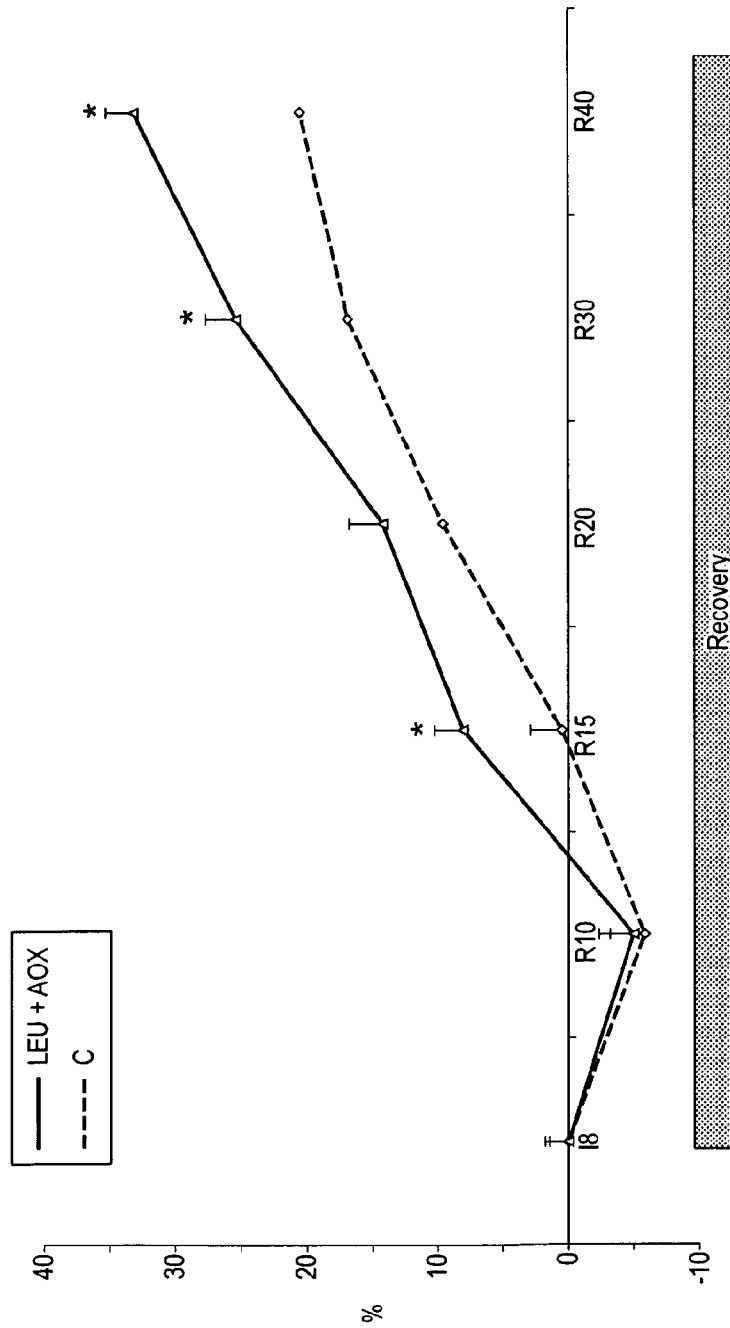
FIG. 2 shows a faster recovery of muscle mass in the immobilized leg from the day I8 of removing the cast in the dietary supplemented group (LEU+AOX) when compared to the control (C) diet group (*: $P<0.05$ for LEU+AOX versus C diets).
Figure 3:
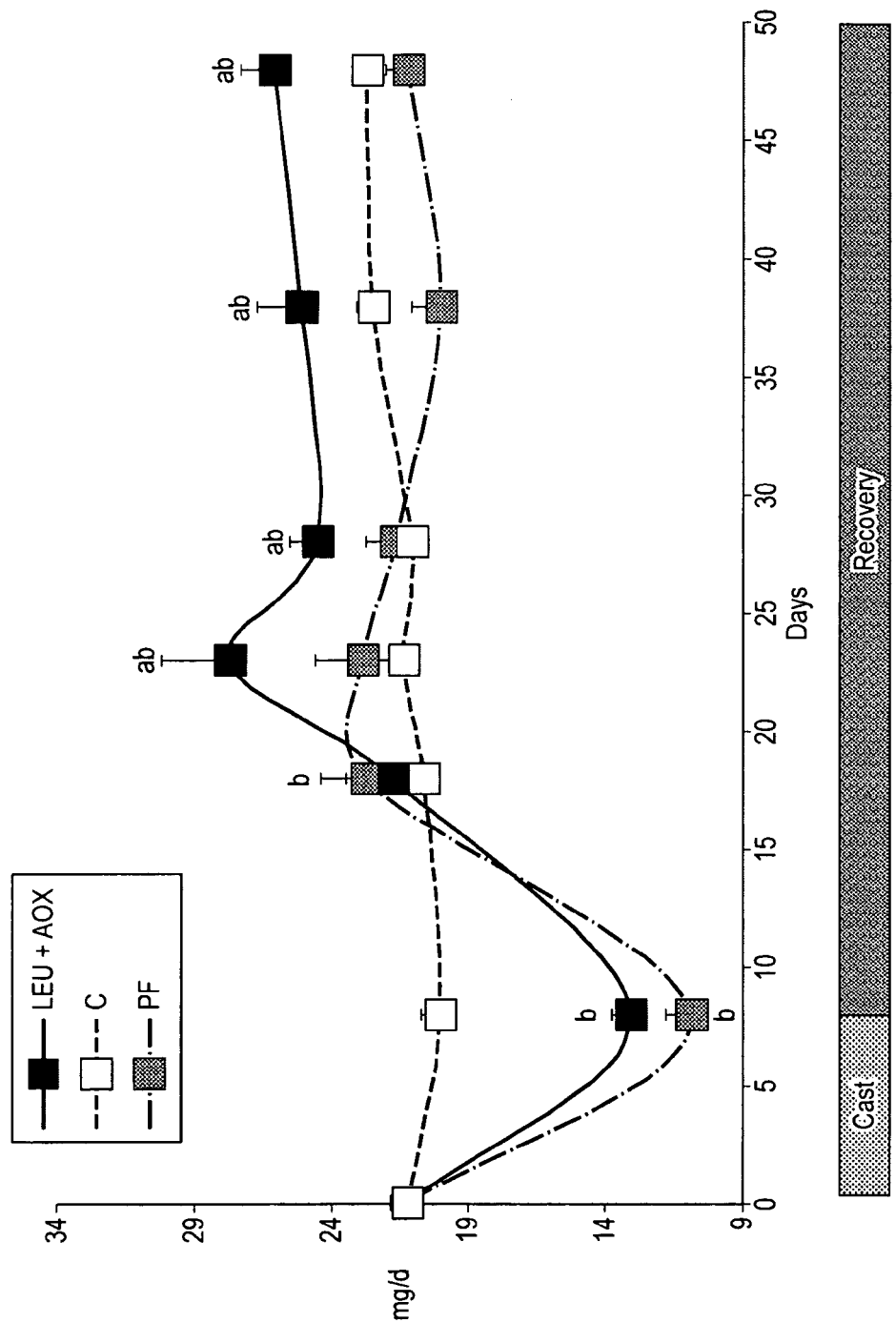
FIG. 3 shows higher muscle protein synthesis rate in the immobilized leg of rat receiving the supplemented diet as compared to the control diet during the recovery period from R15 to R40 (ie from days 23 to 48). This was measured in post absorptive state (a: different from C, b different from PF, $P<0.05$).
Figure 4:
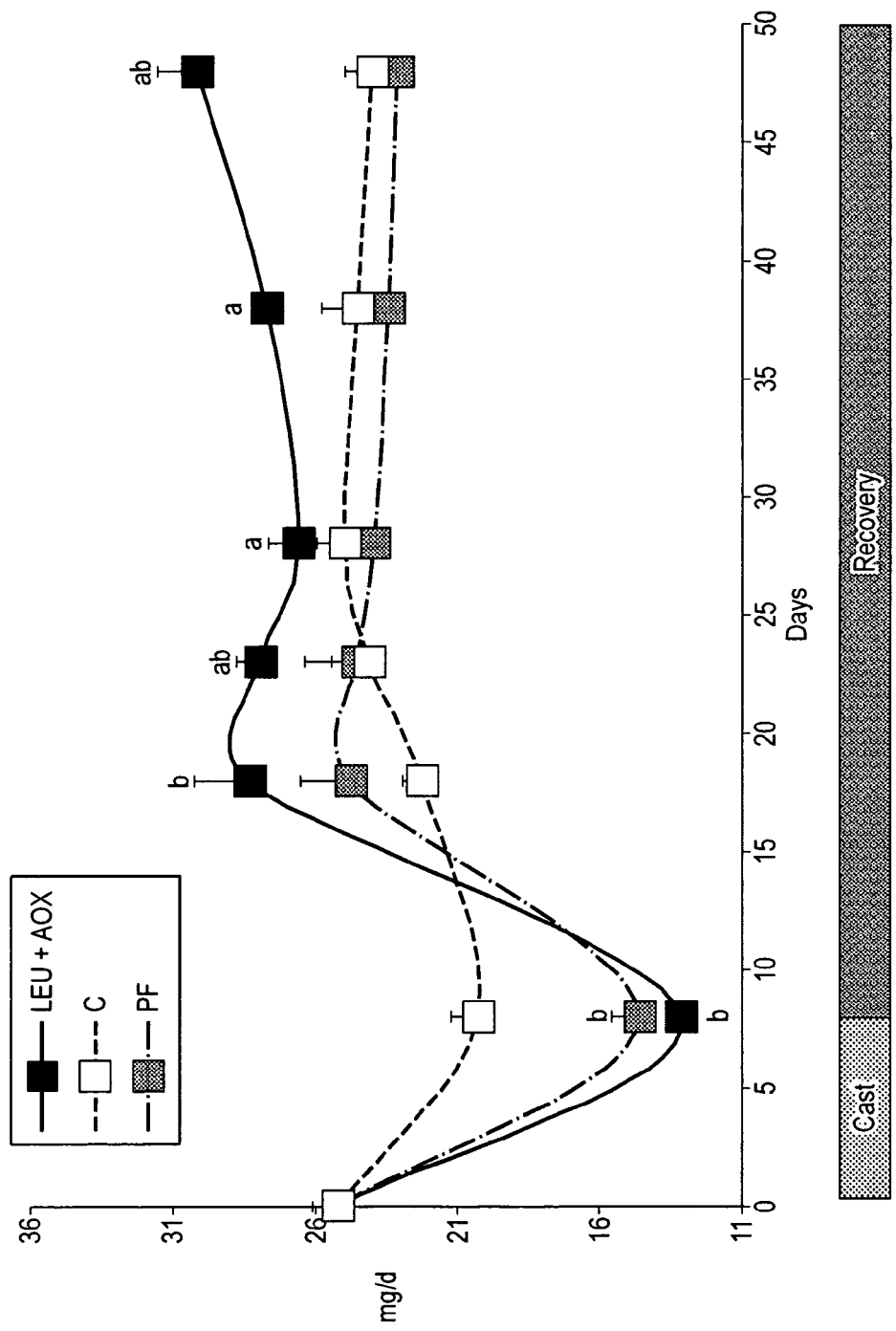
FIG. 4 shows higher muscle protein synthesis rate in the immobilized leg of rat receiving the supplemented diet as compared to the control diet during the recovery period from R15 to R40 (ie from days 23 to 48). This was measured in post prandial state (a: different from C, b different from PF, $P<0.05$).
Figure 5:
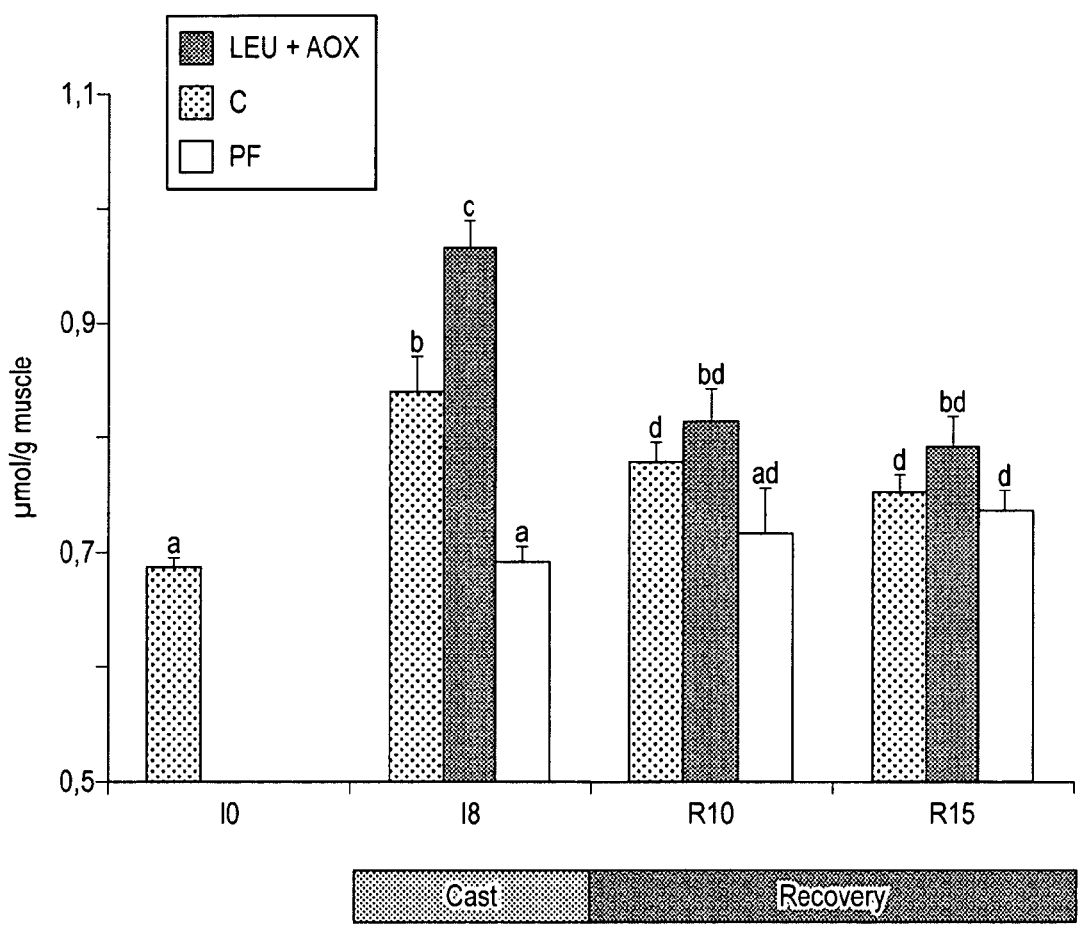
FIG. 5 shows higher intramuscular level of glutathione in the immobilized leg of rat fed the supplemented diet as compared to the control diet on day 10 of recovery. ($P<0.05$ between groups when different letters: a,b,c,d)

Upon receipt, the rats were weighed and placed in individual cages in an environment controlled for temperature (22-23° C.) The animals were placed in a module with reversed lighting (light from 20:00 to 08:00). The animals were fed with the C diet (13% casein) for 1 month before being fed with the experimental diets (according to their group) (FIG. 1).

Food intake and rat body weight was daily recorded.

The day before slaughter the food was removed at 16:30. On slaughtering day, the animals were maintained fasted (PA) or received their respective diets for one hour (PP), then the diet was removed until the time of slaughtering (150-180 min after the diet was given). 40 minutes before slaughter, a $^{13}C$ valine flooding dose (150 μmol/100 g rat; MPE=99%, Intra Venous injection) was performed to assess muscle protein synthesis.

The rats were anesthetized (injection of sodium pentobarbital 50 mg/kg intraperitoneal) and the sampled tissues were weighed, frozen in liquid nitrogen (freeze clamping technique) and stored at −80° C. Blood sampling was performed in the aorta. Gastrocnemius, Tibialis Anterior, Soleus, Extensor Digitorum Longus were dissected in both immobilized and non immobilized legs on each rat.

Protein synthesis was assessed by measuring the 13C valine incorporation into muscle proteins. Free and bound valine enrichments were measured for calculation of protein synthesis rates. Measurement of free $[1-^{13}C]$valine enrichment was done as its t-butyldimethylsilyl derivative by gas chromatography electron impact mass spectrometry, using a HP-5890 gas chromatograph coupled to a HP-5972 organic mass spectrometer quadrupole (Hewlett-Packard, Paris, France). The ions m/z 336 and 337 were monitored. Enrichment of $[1-^{13}C]$valine into muscle proteins was measured as its N-acetyl-propyl derivatives.

After the formation of the N-acetyl-propyl derivative of valine, the ratio $^{13}CO_2:^{12}CO_2$ was measured by gas chromatography-combustion-isotope ratio mass spectrometry (GC-C-IRMS, Isoprime, Cheadle, UK).

The invention claimed is:

1. A method for the treatment of muscle atrophy caused by immobilization and not associated with aging, the method comprising:
administering a first composition to an individual in need thereof, the first composition is administered to the individual daily for a first time period extending from when the immobilization ends to at least 14 consecutive days after the immobilization ends, the first composition comprising leucine in an amount between 2 and 10 weight-% based on total dry weight of the first composition, about 10-50 g isoleucine per kg of the first composition, about 10-50 g valine per kg of the first composition, and at least one antioxidant comprising 0.5 to 1.5 g hesperetine-7-glucoside per kg of the first composition and 1 to 2 g curcumin per kg of the first composition; and
administering a second composition to the individual, the second composition is administered to the individual daily during a second time period starting when the first time period ends, the second composition comprising leucine in an amount between 2 and 10 weight-% based on total dry weight of the second composition, about 10-50 g isoleucine per kg of the second composition, and about 10-50 g valine per kg of the second composition, and at least one of the first and second compositions has at least one different ingredient relative to the other composition.

2. The method of claim 1, wherein the immobilization is caused by bed rest and/or by plastering.

3. The method of claim 1, wherein at least one of the first and second compositions comprises the leucine and the at least one antioxidant in a weight ratio in the range of 25:1 to 1:1.

4. The method of claim 1, wherein at least one of the first and second compositions is administered in an amount corresponding to about 0.03 to 0.2 g leucine per kg body weight.

5. The method of claim 1, wherein at least one of the first and second compositions comprises about 15-30 g isoleucine per kg of the composition and about 15-30 g valine per kg of the composition.

6. The method of claim 1, wherein the leucine is L-leucine in at least one of the first and second compositions.

7. The method of claim 1, wherein the first composition is administered immediately following the immobilization.

8. The method of claim 1, wherein at least one of the first and second compositions is administered via a route selected from the group consisting of orally, enterally, and parenterally.

9. The method of claim 1, wherein the individual is a human or animal.

10. The method of claim 1, wherein at least one of the first and second compositions is selected from the group consisting of food compositions, dietary supplements, nutritional compositions, nutraceuticals, powdered nutritional products to be reconstituted in water or milk before consumption, food additives, medicaments, drinks, and pet food.

11. The method of claim 1, wherein the muscle is a skeletal muscle.

12. The method of claim 1, wherein the at least one antioxidant in the first composition further comprises 1 to 3 g rutin per kg of the composition.

13. The method of claim 1, wherein the at least one antioxidant in the first composition further comprises 4-6 μg Selenium per kg of the composition.

14. The method of claim 1, wherein the at least one antioxidant in the first composition further comprises 90-100 µg Zn per kg of the composition.

15. The method of claim 1, wherein the second time period in which the second composition is administered daily extends at least 21 consecutive days after the first time period ends.

16. The method of claim 1, wherein the at least one antioxidant in the first composition further comprises 1-3 g rutin and 1-3 g green tea catechin per kg of the first composition, and the second composition is lacking at least one of hesperetine-7-glucoside, curcumin, rutin or green tea catechin.

17. The method of claim 16, wherein the second composition is lacking green tea catechin.

18. The method of claim 16, wherein the second composition is lacking hesperetine-7-glucoside, curcumin, rutin and green tea catechin.

19. The method of claim 1, wherein at least one of the first and second compositions comprises casein.

20. The method of claim 1, wherein both of the first and second compositions comprise casein.

\* \* \* \* \*